United States Patent [19]

Herold

[11] 4,189,065
[45] Feb. 19, 1980

[54] METERING DISPENSER FOR HIGH-VISCOSITY COMPOSITIONS

[75] Inventor: Wolf-Dietrich Herold, Herrsching, Fed. Rep. of Germany

[73] Assignee: ESPE Fabrik Pharmazeutischer Praeparate GmbH, Fed. Rep. of Germany

[21] Appl. No.: 761,958

[22] Filed: Jan. 24, 1977

[30] Foreign Application Priority Data

Feb. 4, 1976 [DE] Fed. Rep. of Germany ... 7603096[U]

[51] Int. Cl.² .......................... G01F 11/00; B67D 5/42
[52] U.S. Cl. ...................................... 222/46; 222/390; 128/236
[58] Field of Search ..................... 128/236; 239/324; 401/172–174; 222/39, 41, 44, 46, 48, 390

[56] References Cited

U.S. PATENT DOCUMENTS

| 1,644,173 | 10/1927 | Carr | 222/390 |
| 1,751,139 | 3/1930 | Feinstein | 128/236 X |
| 2,745,575 | 5/1956 | Spencer | 222/390 X |
| 3,353,718 | 11/1967 | McLay | 222/390 X |

FOREIGN PATENT DOCUMENTS

| 585633 | 3/1925 | France | 222/390 |
| 56006 | 3/1934 | Norway | 222/390 |

*Primary Examiner*—David A. Scherbel
*Attorney, Agent, or Firm*—Ostrolenk, Faber, Gerb & Soffen

[57] ABSTRACT

A dispensing device for high-viscosity compositions includes a hollow cylindrical body in which the composition is contained between a closeable discharge opening at the front end of the body and a piston movable in the longitudinal direction of the body. The piston is driven by a threaded spindle engaging a threaded nut and bearing with its front end against the rear face of the piston. The nut is slid in a direction transverse to the longitudinal axis of the body into engagement with a flange provided at the rear end of the body. A detent mounted on the nut cooperates with a longitudinal groove provided on the spindle to indicate the angular position of the spindle, thus the amount of composition being discharged, in addition to preventing the spindle from reverse rotation.

11 Claims, 7 Drawing Figures

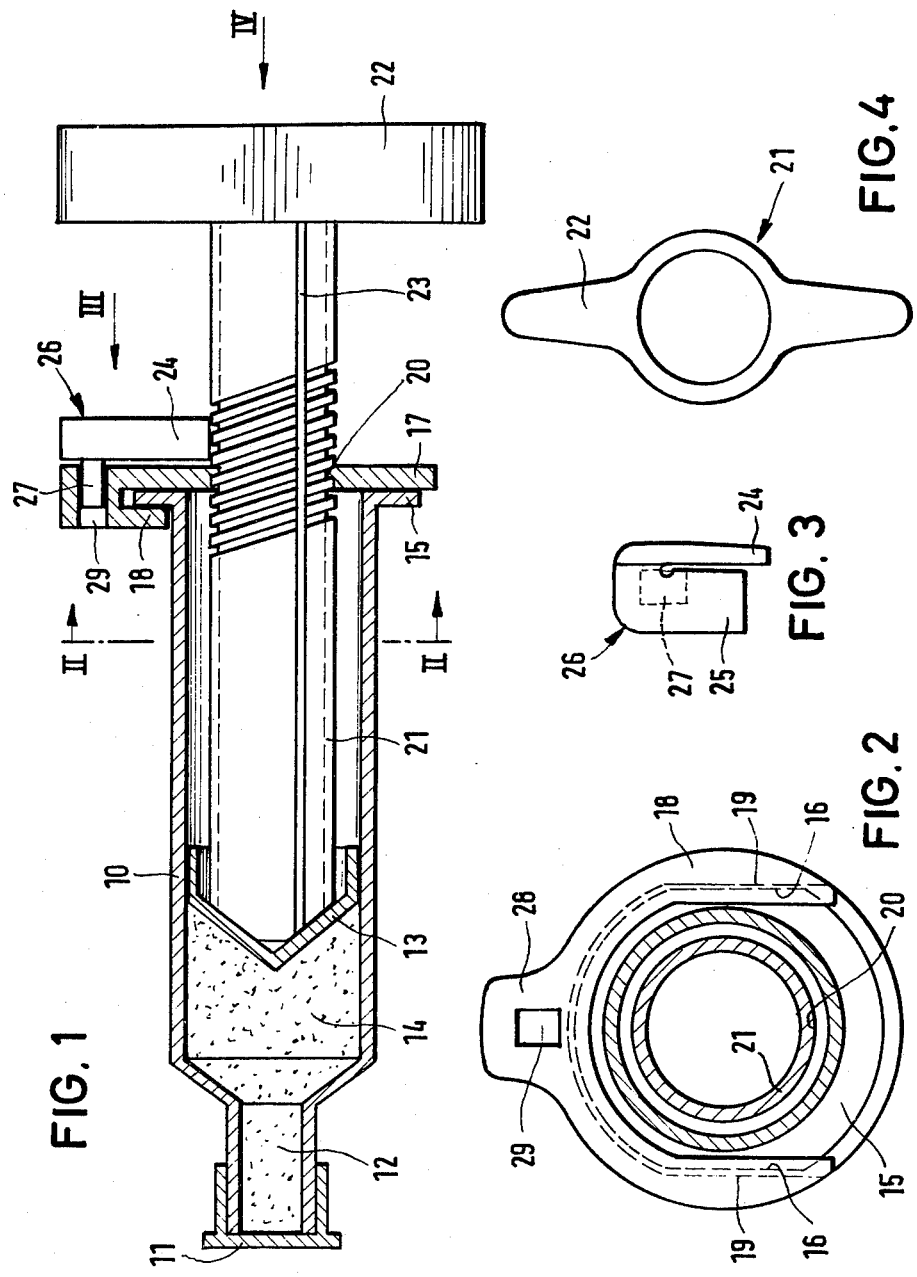

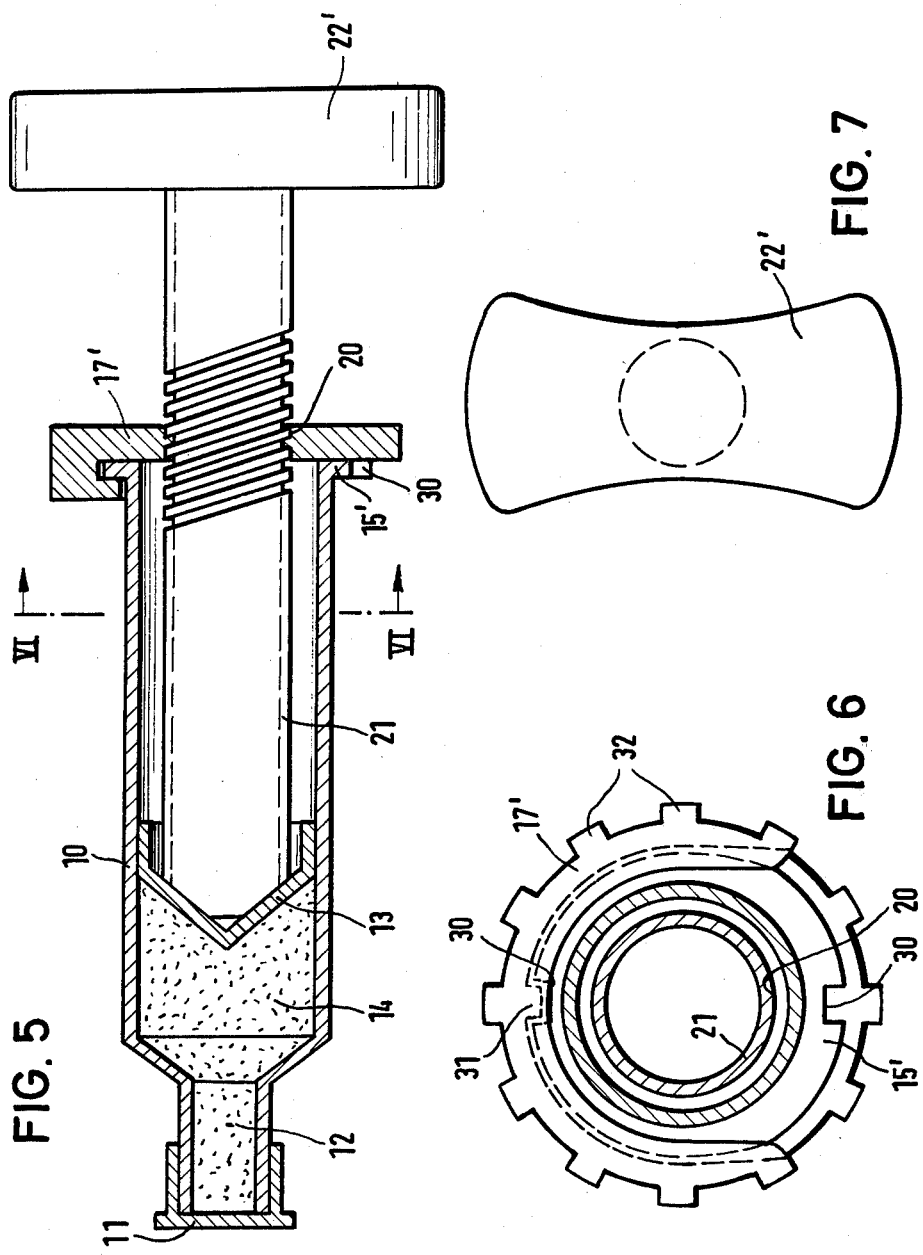

METERING DISPENSER FOR HIGH-VISCOSITY COMPOSITIONS

BACKGROUND OF THE INVENTION

This invention relates to a dispensing device for metering high-viscosity compositions. Devices of this type are for example used for the individual components of a polymer for dental applications. As both the final hardness and the setting time of such a polymer may depend on the mixture ratio, an accurate metering of the individual components is essential. The metering must be the more accurate the smaller the desired amounts are. This requirement typically occurs again in dental applications where small amounts of a substance, such as a molding composition, are often required. However, the invention is not limited to this specific application. It is useful also in cases where the requirements as to metering accuracy are not quite as high but where a dispensing device for metering high-viscosity compositions is desired which is easy to handle and to manufacture.

U.S. Pat. No. 3,873,008 discloses a device in which the high-viscosity composition is contained within in an elongate hollow body between a closeable discharge opening provided at the front end of the hollow body and a piston movable in the longitudinal direction by means of a threaded spindle. The spindle engages a nut mounted on the rear end of the hollow body with the front end of the spindle bearing against the rear side of the piston. A flange provided on the nut has indicia which cooperate with a linear groove formed on the threaded spindle to provide a control of the angular position, thus of the rotation covered by the spindle. As the piston is driven forwardly by the treaded spindle, the amount of composition being dispensed may be controlled by watching the groove and the indicia, the metering accuracy being dependent on how exact the groove is set to the respective indicia. Accurate metering thus requires careful handling of the device. There is also a chance of the spindle being screwed out of the hollow body due to careless handling, inadvertent actuation or shock, resulting in an amount corresponding to only an incomplete revolution being dispensed by a subsequent rotation of the spindle about accurately one complete revolution.

In the device of the above-mentioned U.S. patent 3,873,008, the threaded ring or nut which guides the threaded spindle is pressed in the axial direction over a bead provided at the rear end of the hollow body. Unless the manufacturing tolerances of the various individual components are closely observed, there is a danger that the nut occasionally rotates with the spindle and relatively to the hollow body. When this occurs, the operator is uncertain about the amount dispensed although the relationship between the dispensed amount and the indicia is not changed. The mechanism advancing the piston is of course partially or completely ineffective in such a case.

As a further difficulty encountered with the known device, unallowable production tolerances affecting the engagement between the nut and the hollow body entail the danger that actuation of the spindle may separate the nut from the rear end of the hollow body rather than advancing the piston within the body. This danger occurs particularly in case the composition to the dispensed has a very high viscosity which is true with thermoplastic substances at low temperatures.

It is an object of the invention to provide a device which allows precise metering by simple means. A further object of the invention resides in achieving an exact metering by means of a device which is easy to handle. It is another object of the invention to provide a device for dispensing high-viscosity compositions which is easy to manufacture and safe to handle. A further object of the invention is a device for dispensing high-viscosity compositions which functions safely and largely independently from production tolerances.

SUMMARY OF THE INVENTION

A dispensing device for metering high-viscosity compositions in accordance with the present invention comprises an elongate hollow body for receiving the composition between a closeable discharge opening provided at the front end of the hollow body and a piston adapted to be moved by a threaded spindle in the longitudinal direction of the hollow body. The threaded spindle engages a nut mounted on the rear end of the hollow body and bears with its front end against the rear side of the piston. According to one aspect of the invention, the threaded spindle includes a longitudinal groove for indicating its angular position relative to the nut, with a detent being mounted on the nut for snap-engagement with the longitudinal groove. This provides an indication which is not only visible but also audible and sensible. An exact metering is thus possible even without visually watching the threaded spindle so that the operator may concentrate his attention to the location where the composition is dispensed from the front end of the hollow body. The snap-action additionally impedes any inadvertent rotation of the spindle due to careless handling of the device.

The detent is preferable adapted to form a positive stop against rotation of the spindle in the reverse sense, thereby ensuring that the spindle is always rotated by an accurately defined angle, particularly by a complete revolution, and that the complete amount of composition corresponding to such angle is thereby discharged.

According to another aspect of the invention, the nut which guides the threaded spindle is fixed to the rear end of the hollow body by being slid in a direction transverse of the longitudinal axis of the hollow body into engagement with a flange integrally formed with the body. This mounting ensures that even great reaction forces occurring due to a particularly high viscosity of the composition to be dispensed or with adverse tolerances of the components will not separate the nut from the rear end of the hollow body. In the lateral direction, the nut is at the same time secured by the penetrating spindle. The formation of a nut which is slid into engagement in the lateral direction, also results in a particularly easy assembly which may readily be automized without great expense.

The nut and the flange integrally formed on the hollow body are preferably so shaped that the nut is prevented from being rotated by the threaded spindle.

In another preferred embodiment, the threaded spindle has a square thread which not only results in a low friction between the spindle and the nut but also reduces the danger of the thread being damaged by the detent if provided.

In a further advantageous embodiment, the rear ends of the threaded spindle carries an elongate actuation handle to provide the operator with a feeling for the angular position and the rotation covered by the threaded spindle, thereby rendering the metering still easier. One complete revolution of the spindle will usually be produced by two subsequent manupulations.

BRIEF DESCRIPTION OF THE DRAWINGS

Further objects, advantages and details of the invention will become apparent from the following specification of preferred embodiments with reference to the drawings. In the drawings FIG. 1 is a longitudinal section through an assembled device according to a first embodiment;

FIG. 2 is a cross section along the line II—II of FIG. 1;

FIG. 3 is an end view of a portion of the device taken in the direction of the arrow III in FIG. 1;

FIG. 4 is an end view of another portion of the device taken in the direction of the arrow IV in FIG. 1;

FIG. 5 is a longitudinal section similar to FIG. 1 through the device according to another embodiment of this invention;

FIG. 6 is a cross section along the line VI—VI of FIG. 5; and

FIG. 7 is an end view similar to FIG. 4 showing another embodiment of the respective portion of the device.

DETAILED DESCRIPTION OF PREFERRED EMBODIMENTS

Referring to FIGS. 1 to 4, the main portion of the device is formed by an elongate cylindrical hollow body 10 including a front end which conically tapers towards a discharge opening 12 closeable by a cap 11. A piston 13 slidable within the body 10 consists of a cylindrical hollow portion having a conical apex. The conical shape of the piston apex corresponds to the conical shape of the front end of the body 10 to ensure substantially complete discharge of the pasty composition 14 contained in the body 10 in front of the piston 13.

The body 10 has at its rear end a flange 15 provided with two flattenings 16 disposed diametrically oppositely of each other, as shown in FIG. 2. A nut 17 is slid onto this flange 15 in a direction perpendicular to the longitudinal axis of the body 10, with a flange 18 of the nut 17 engaging behind the flange 15 of the body 10. Inside the flange 18, the nut 17 has a pair of flat portions 19 disposed diametrically oppositely to each other, which are complementary to, and cooperate with, the flattenings 16 of the flange 15 to prevent relative rotation between the hollow body 10 and the nut 17.

A central threaded bore 20 is provided in the nut 17 which engages a threaded spindle 21. The bore 20 and the spindle 21 are provided with square threads. The front end of the threaded spindle 21 bears against a rear face of the piston 13, and the rear end of the spindle 21 is provided with a handle 22 preferably in the form of a tommy as shown in FIG. 4.

The spindle 21 which is again formed as a hollow cylinder for saving material, has a longitudinal groove 23 extending over the entire axial length of the spindle 21 and having a depth which may be substantially equal to the depth of the thread. The tip of a resilient member 24 is mounted to cooperate with the groove 23, the resilient member 24 and a stop member 25 together forming a detent generally designated 26. Formed integrally with the detent 26 is a pin 27 for mounting the detent in an aperture 29 provided in an extension 28 of the flange 18. The pin 27 and the aperture 29 have an angular cross section to prevent the detent 26 from rotating with respect to the nut 17.

The detent 26 is mounted on the nut 17 so that the resilient member 24 resiliently bears on the spindle 21, the resilient member 24 extending at such an angle with respect to the radial direction that the member 24 is lifted out of the groove 23 when the spindle 21 is screwed into the body 10, while the groove 23 will engage the resilient member 24 and force it against the stop member 25 when it is tried to rotate the spindle 21 in the opposite sense. The width of the resilient member 24 in the axial direction of the threaded spindle 21 equals at least about one pitch of the thread to prevent the tip of the member 24 from becoming jammed in the thread.

In a basic position, the resilient member 24 of the detent 26 engages the groove 23. For discharging the pasty composition 14 contained in the body 10, firstly the cap 11 is removed. The threaded spindle 21 is then rotated forwardly by means of the handle 22 until the detent 26 again snaps into the groove 23. At this moment, one complete revolution has been performed provided only one groove 23 is formed on the spindle 21. The piston 13 has thereby been moved an according distance within the body 10 and has pressed out of the discharge opening 12 an accurately metered amount of the composition 14. The amount dispensed with each one revolution is defined by the inner diameter of the hollow body 10 and the pitch of the thread.

In the embodiment of FIGS. 1 to 4, the spindle 21 has one single longitudinal groove 23. For metering a unit amount, a complete revolution is thus required which is conveniently performed by two subsequent manipulations of the tommy-like handle 22. For metering smaller amounts, two or more longitudinal grooves may be equi-angularly distributed on the spindle 21.

With two longitudinal grooves disposed diametrically opposite to each other, the handle 22 has preferably the same shape as shown in FIG. 4, while with three grooves a handle would be preferable which has three tommy-like projections disposed at angles of 120°. When the handle thus corresponds to the respective prescribed rotational angle of the spindle 21, a feeling of the respective angle being covered is provided in addition to the visible, audible and sensible snapping of the detent 26 into the groove 23.

The embodiment shown in FIGS. 5 to 7 differs from that of FIGS. 1 to 4 basically in that the spindle 21 has no longitudinal grooves and that no detent cooperating with such grooves is provided. In FIGS. 5 to 7 the same reference numbers as in FIGS. 1 to 4 are used, with the modified components being identified by primed reference symbols.

Referring to FIGS. 5 and 6, the flange 15' provided at the rear end of the hollow body 10 is provided with two recesses 30 disposed diametrically oppositely to each other instead of the flattenings 16 of FIG. 2. Only one such recess 30 or even three or more recesses may be provided at the periphery of the flange 15'. According to FIG. 6, the nut 17' is slid onto the flange 15' such that a nose 31 provided inside the nut engages any one of the recesses 30 to prevent relative rotation between the nut 17' and the body 10. At its outer periphery the nut 13' is formed with a plurality of projections 32 which not only enhance the grip but also provide an additional orientation about the rotational angle covered by the handle 22' with respect to the nut 17'. The handle 22' may have the shape shown in FIG. 7 rather than that of FIG. 4.

The embodiment of the invention shown in FIGS. 5 to 7 is intended for those applications where not such a precise metering is required as is achieved by the device of FIGS. 1 to 4. The nut 17' being slid onto the flange 15' transversely of the direction in which the pressure acts, and being secured against sliding off the flange by the spindle 21 penetrating the nut 17' renders the device suitable for dispensing high-viscosity compositions without the danger that the nut 17' is separated from the rear end of the body 10 due to the reaction force created upon actuation of the threaded spindle.

The features shown in the various figures are partly interchangeable. For instance, the handle 22' may be used in the embodiment of FIG. 1. Similarly, the locking against rotation between the nut and the flange shown in FIG. 2 may be used in the embodiment of FIG. 5. On the other hand, the outer projections 32 formed on the nut 17' of FIG. 6 are particularly useful in the embodiment having no groove and detent as shown in FIGS. 5 and 6, because the detent 26 and the extension 28 on the nut as provided in the embodiment of FIGS. 1 to 4 achieve the desired metering orientation in addition to an improved grip.

What is claimed is:

1. A dispensing device for metering high-viscosity compositions comprising an elongate hollow body having a discharge opening at its front end, a piston disposed within the body for movement in the longitudinal direction thereof, the composition being contained between said piston and said discharge opening, a nut mounted on the rear end of the body, means preventing rotation of said nut relative to said body, a threaded spindle engaging said nut so as to be rotatable relatively to said body and bearing with its front end against the rear side of said piston, said spindle having at least one longitudinal groove, and detent means mounted on said nut for providing a snap-action with said at least one groove thereby indicating the angular position of said spindle relative to said nut.

2. The device of claim 1, wherein said detent means is adapted to prevent a screwing of said threaded spindle out of the body.

3. The device of claim 1, comprising a flange formed at the rear end of the body, said nut being adapted to be slid onto said flange in a direction transversely of said longitudinal axis of the body.

4. The device of claim 1, wherein said threaded spindle has a square thread.

5. The device of claim 1, wherein said spindle carries at its rear end an elongate actuation handle.

6. A dispensing device for metering high-viscosity compositions comprising an elongate hollow body having a discharge opening at its front end, a piston disposed within the body for movement in a longitudinal direction thereof, the composition being contained between said piston and said discharge opening, a nut mounted on the rear end of the body, a threaded spindle engaging said nut and bearing with its front end against the rear side of said piston, said spindle having at least one longitudinal groove for indicating the angular position of said spindle relative to said nut, and detent means comprising a pawl mounted on the rear side of said nut, the pawl including a resilient member adapted to snap into said at least one groove of said spindle and a stop member for limiting a rotation of said resilient member against a prescribed rotational direction of said threaded spindle.

7. The device of claim 6, wherein said pawl includes a pin having a non-circular cross section, said pin engaging a complementary aperture provided in said nut.

8. The device of claim 6, wherein said threaded spindle has a square thread.

9. A dispensing device for metering high-viscosity compositions comprising an elongate hollow body having a discharge opening at its front end, a piston disposed within the body for movement in the longitudinal direction thereof, the composition being contained between said piston and said discharge opening, a nut mounted on the rear end of the body, a threaded spindle engaging said nut and bearing with its front end against the rear side of said piston, said spindle having at least one longitudinal groove for indicating the annular position of said spindle relatively to said nut, and detent means mounted on said nut for cooperating with said at least one groove; said device having a flange formed at the rear end of the body, said nut being adapted to be slid onto said flange in a direction transversely of said longitudinal axis of the body; said flange having lateral flattenings extending parallel to said transverse direction and said nut has corresponding flat portions for engagement by said flattenings.

10. A dispensing device for metering high-viscosity compositions, comprising an elongate hollow body having a discharge opening at its front end, a piston disposed within the body for movement along the longitudinal direction thereof, the composition being contained within the body between said piston and said discharge opening, a flange formed at the rear end of the body, a nut slid into engagement with said flange in a direction transverse of said longitudinal axis of the body, and a threaded spindle engaging said nut and bearing with its front end against the rear side of said piston; wherein said flange has at least one recess and said nut has a projection for engagement with said at least one recess.

11. The device of claim 10, wherein said nut is formed on its outer periphery with a plurality of projections.

* * * * *